US00PP31512P2

(12) United States Plant Patent
Kleinwee

(10) Patent No.: US PP31,512 P2
(45) Date of Patent: Mar. 3, 2020

(54) ***CHRYSANTHEMUM* PLANT NAMED 'CIFZ0060'**

(50) Latin Name: ***Chrysanthemum* x *morifolium***
Varietal Denomination: CIFZ0060

(71) Applicant: SYNGENTA PARTICIPATIONS AG, Basel (CH)

(72) Inventor: Theodorus Cornelis Maria van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,524

(22) Filed: Mar. 9, 2018

(51) Int. Cl.
*A01H 5/02* (2018.01)
*A01H 6/14* (2018.01)

(52) U.S. Cl.
USPC ..... Plt./298

(58) Field of Classification Search
USPC ..... Plt./286, 298
See application file for complete search history.

*Primary Examiner* — Susan McCormick Ewoldt
(74) *Attorney, Agent, or Firm* — Dale Skalla

(57) ABSTRACT

A new garden type *Chrysanthemum* plant named 'CIFZ0060' particularly distinguished by its round mound plant habit, a medium size, red decorative flower color and a natural season response in mid to late September.

1 Drawing Sheet

Figure 1:
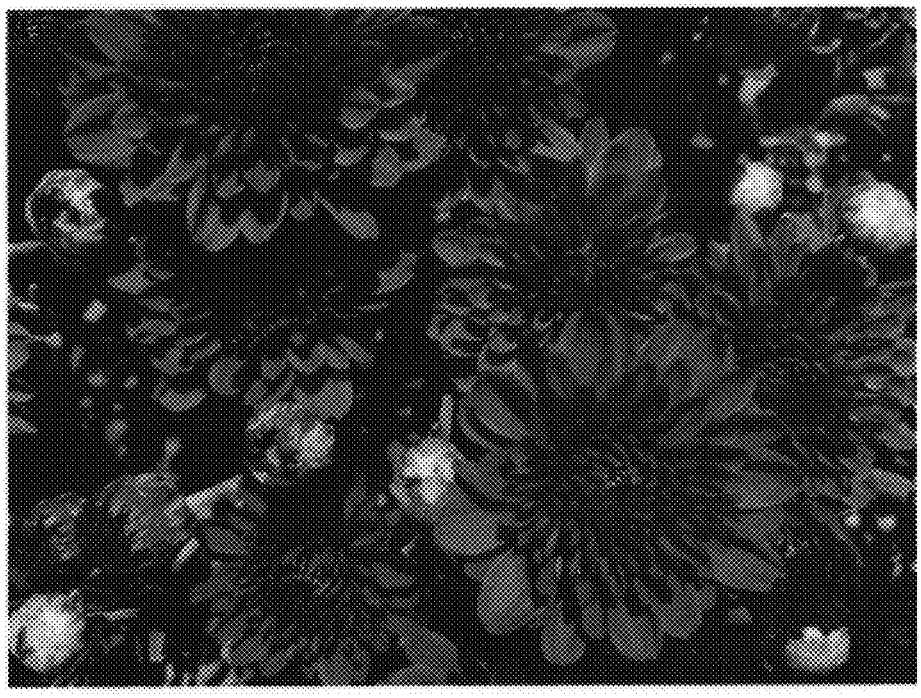

Latin name of the genus and species of the plant claimed: *Chrysanthemum* x *morifolium.*

Varietal denomination: 'CIFZ0060'.

BACKGROUND OF THE NEW PLANT

The present invention comprises a new *Chrysanthemum*, botanically known as *Chrysanthemum* x *morifolium*, and hereinafter referred to by the variety name 'CIFZ0060'.

'CIFZ0060' is a product of a planned breeding program. The new cultivar has medium size plant with round mound plant habit, a medium size, red decorative flower color and a natural season response in mid to late September.

'CIFZ0060' originated from a cross made in February 2013 in Enkhuizen, the Netherlands. Seeds were sown in June 2013 in Enkhuizen, The Netherlands and 'CIFZ0060' was selected from the resulting population on Nov. 1, 2013 in Enkhuizen, the Netherlands The female parent was the unnamed selection of proprietary line 08-M185. When compared to the female parent, 'CIFZ0060' has:

1) Smaller flower size with more disk florets and no petal quill and red not dark pink/lavender flower color like the female parent.
2) Blackcloth response is a half a week slower, and natural season response is almost two weeks slower than the female parent
3) Similar plant habit and size compared to female parent The male parent was the unnamed seedling of proprietary line 07-M168. When compared to the male parent, 'CIFZ0060' has:

1) Similar flower size and color but less disk florets than the male parent
2) Blackcloth response is similar but natural season response is about a half a week faster than the male parent
3) Similar plant size and plant habit as the male parent The first act of asexual reproduction of 'CIFZ0060' was accomplished when vegetative cuttings were propagated from the initial selection in January 2014 in Enkhuizen, the Netherlands

BRIEF SUMMARY OF INVENTION

Horticultural examination of plants grown from cuttings of the plant initiated in January 2014 and continuing thereafter, has demonstrated that the combination of characteristics as herein disclosed for 'CIFZ0060' are firmly fixed and are retained through successive generations of asexual reproduction.

'CIFZ0060' has not been observed under all possible environmental conditions. The phenotype may vary significantly with variations in environment such as temperature, light intensity and day length.

A Plant Breeder's Right for this cultivar has not been applied for. 'CIFZ0060' has not been made publicly available prior to the effective filing date of this application, notwithstanding any disclosure that may have been made less than one year prior to the effective filing date of this application by the inventor or another who obtained 'CIFZ0060' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0060' with colors being as true as possible with an illustration of this type.

Figure 2:
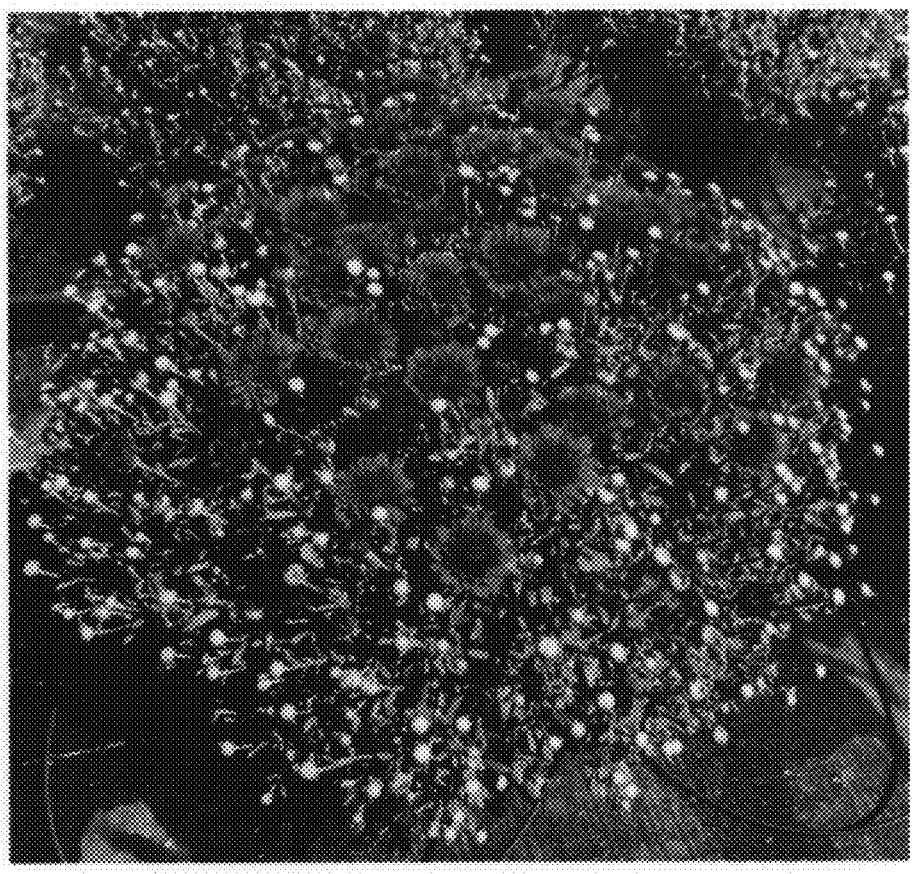

The photographic drawings show in FIG. 1 a close view of flower of the new variety and in FIG. 2 a flowering plant from an outdoor trial.

The aforementioned photographs: FIG. 1 and FIG. 2 were taken in October 2017 both showing a plant from the same natural flowering outdoor trial in Gilroy, Calif. These plants were about 10 weeks of age. One rooted cutting per pot had been planted in a one gallon pot, not pinched in week 35. Plants started flowering late October.

DETAILED BOTANICAL DESCRIPTION

The measurements were taken in Gilroy, Calif. in October 2017 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0060' AND TWO MOST SIMILAR VARIETIES:

| | 'CIFZ0060' | 'Yotabitha', U.S. Plant Pat. No. 16,110 (Tabitha Scarlet) |
|---|---|---|
| Flowering response (blackcloth): | Blackcloth response and natural season response is similar but under higher temperatures 'CIFZ0060' can flower up to a week faster than 'Tabitha Scarlet' | Blackcloth response and natural season response is similar but under higher temperatures 'Tabitha Scarlet' can flower up to a week slower than 'CIFZ0060' |
| Flowering habit: | More uniform flowering | More uniform flowering |
| Flower color: | Darker red color | Lighter red (scarlet) color |
| Flower size: | Similar to a bit smaller | Similar to a bit bigger |
| Flower type: | More disc florets | Less disc florets |
| Plant habit or size: | Similar plant height but wider plant width than 'Tabitha Scarlet' | Similar plant height but more upright than 'CIFZ0060' |

TABLE 2

| | 'CIFZ0060' | 'Gedi Two Cam' - U.S. Plant Pat. No. 14,472 (Camina) |
|---|---|---|
| Flowering response (blackcloth): | Similar | Similar |
| Flowering response (natural): | Similar | Similar |
| Flower type: | More disc florets | Less disc florets |
| Flower longevity: | Longer lasting | Shorter lasting |
| Flower size: | Smaller | Bigger |
| Plant habit or size: | Similar, but wider plant | Similar, but more upright plant |

Plant:

*Form, growth and habit.*—Herbaceous garden-type, stems upright and outwardly spreading, freely branching, strong and moderately vigorous growth habit.

*Plant height (above soil).*—15-18 cm.

*Plant height (inflorescence included).*—18-24 cm.

*Plant width.*—38-43 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 139A.

*Immature leaf, color lower surface.*—RHS 137B.

*Mature leaf, color, upper surface.*—RHS 139A.

*Mature leaf, color lower surface.*—RHS 137B.

*Length.*—4.5-5.0 cm.

*Width.*—3.8-4.4 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138B.

*Color of veins, lower surface.*—RHS N138B.

*Pattern of veining.*—Palmate.

*Petiole color.*—RHS 138A.

*Petiole length.*—1.4-1.8 cm.

*Diameter.*—0.2 cm.

*Texture.*—Covered with bifid hairs.

Stem:

*Quantity of main branches per plant.*—6 to 8.

*Color of stem.*—RHS 137A overlain with RHS 187B.

*Length of stem.*—8-12 cm.

*Diameter.*—0.5 cm.

*Length of internodes.*—0.5-1.0 cm.

*Texture.*—Bifid hairs.

*Color of peduncle.*—RHS 137A overlain with RHS 187B.

*Length of peduncle.*—4.5-5.0 cm.

*Peduncle diameter.*—0.2 cm.

*Texture.*—Bifid hairs.

Inflorescence:

*Type.*—Compositae, solitary, semi-double to double type inflorescences borne terminally above foliage, ray and disc florets arranged on a capitulum.

*Quantity of short days to flowering (response time).*—5 to 5½ weeks.

*Natural season flowering.*—Mid to late September.

*Quantity of inflorescences per plant.*—150-180.

*Lastingness of individual blooms on the plant.*—About five weeks from first color.

*Fragrance.*—Slightly spicy.

Bud (when showing color):

*Color.*—Closest to RHS 197A.

*Length.*—1.0-1.2 cm.

*Width.*—1.0-1.2 cm.

*Shape.*—Oblate.

Immature inflorescence:

*Diameter.*—3.4-3.6 cm.

*Color of ray florets, upper surface.*—Between RHS 187A and RHS 187B.

*Color of ray florets, lower surface.*—Between RHS 187B and RHS 187C.

Mature inflorescence:

*Diameter.*—5.3-5.8 cm.

*Depth.*—1.2-1.4 cm.

*Total diameter of disc.*—0.4-0.6 cm.

*Receptacle color.*—RHS 145A.

*Receptacle height.*—0.2 cm.

*Receptacle diameter.*—0.4 cm.

Ray florets:

*Average quantity of florets.*—Between 240 and 280 in several whorls.

*Color of florets, upper surface (abaxial).*—Between RHS 187B and 187C.

*Color inner surface* (*adaxial*).—Closest to RHS 187C.
*Length*.—1.6-1.8 cm.
*Width/diameter*.—0.4-0.5 cm.
*Shape*.—Elliptical.
*Apex shape*.—Most obtuse and dentate.
*Base shape*.—Tube.
*Margin*.—Entire, small incisions may occur at the tip.
*Texture, upper surface*.—Papillate.
*Lower surface*.—Papillate.

Disc florets: Approximately 50.
*Width*.—0.5 cm.
*Length*.—3 cm.
*Color*.—RHS 187B at apex, RHS 1B with RHS N145A at base.

Phyllaries:
*Quantity*.—16-20.
*Color, upper surface*.—RHS 138B.
*Color, lower surface*.—RHS 138A.
*Length*.—1.0-1.3 cm.
*Width*.—0.2-0.3 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.3-0.5 cm.
*Style color*.—RHS 150B.
*Style length*.—0.2-0.3 cm.
*Stigma color*.—RHS 13B.
*Stigma shape*.—Bi-parted.
*Ovary color*.—RHS 145B.
*Ovary length*.—0.2 cm.
*Ovary width*.—0.1 cm.

Androecium:
*Stamens*.—1, found on only disc florets.
*Color of filaments*.—RHS 2C.
*Length filaments*.—0.2-0.3 cm.
*Anther color*.—RHS 13C.
*Anther length*.—0.2 cm.
*Anther shape*.—Oval to club shaped.
*Color of pollen*.—RHS 13C.
*Pollen amount*.—Moderate.
*Fertility/seed set*.—Has not been determined to date.
*Disease/pest resistance*.—Has not been determined to date.

What is claimed is:

1. A new and distinct variety of *Chrysanthemum* plant named 'CIFZ0060' substantially as illustrated and described herein.

* * * * *